United States Patent [19]

Sandstrom et al.

[11] Patent Number: 5,882,912
[45] Date of Patent: Mar. 16, 1999

[54] RETROVIRUS ISOLATED FROM HUMANS

[75] Inventors: Paul A. Sandstrom, Decatur, Ga.; Jennifer Brown, Denver, Colo.; Thomas M. Folks, Lithonia, Ga.; Walid Heneine, Decatur, Ga.; William M. Switzer, Stone Mountain, Ga.

[73] Assignee: Center For Disease Control And Prevention, Atlanta, Ga.

[21] Appl. No.: 798,071

[22] Filed: Feb. 12, 1997

[51] Int. Cl.$^6$ .............................. C12N 7/00; C12N 15/00
[52] U.S. Cl. ...................................... 435/235.1; 435/320.1
[58] Field of Search .............................. 435/320.1, 235.1; 514/44

[56] References Cited

U.S. PATENT DOCUMENTS

| | | | |
|---|---|---|---|
| 5,108,920 | 4/1992 | Ng et al. | 435/239 |
| 5,459,056 | 10/1995 | Powell et al. | 435/240.2 |
| 5,597,896 | 1/1997 | Montagnier et al. | 530/388.35 |

OTHER PUBLICATIONS

Hooks et al. The foamy viruses. Bacteriological Reviews, vol. 39, No. 3, pp. 169–185. Sep. 1975.

Schweizer et al. Simian foamy viruses isolated from an accidentally infected human individual. J. of Virol; vol. 71, No. 6, pp. 4821–4824.

"Detection Of Reverse Transcriptase By A Highly Sensitive Assay In Sera From Persons Infected With Human Immunodeficiency Virus Type 1", Walid Heneine, et al., *The Journal of Infectious Diseases,* May 1995, pp. 1210–1216.

"Spumaviruses", Philip C. Loh, *The Retroviridae,* vol. 2, 1993, pp. 361–397.

Cell tropism of the simian foamy virus type 1 (SFV–1), Ayalew Mergia et al., *Journal of Medical Primatology,* Jul. 21, 1995, pp. 2–7.

"Isolation of Novel Human Endogenous Retrovirus–Like Elements with Foamy Virus–Related *pol* Sequence," Agnes Cordonnier et al., *Journal of Virology,* vol. 69, No. 9, Sep. 1995, pp. 5890–5897.

"Identification and Characterization of the Bel 3 Protein of Human Foamy Virus", Jakob Weissenberger and Rolf M. Flugel, *Aids Research and Human Retroviruses,* vol. 10, No. 5, 1994.

"Human Foamy Virus Polypeptides: Identification of *env* and *bel* Gene Products", Marie–Louise Giron et al., *Journal of Virology,* vol. 67, No. 6, Jun. 1993, pp. 3596–3600.

"Isolation, Cloning, and Sequencing of Simian Foamy Viruses from Chimpanzees (SFVcpz); High Homology to Human Foamy Virus (HFV)", Ottmar Herchenroder et al., *Virology* 201, 1994, pp. 187–199.

"Isolation of a New Foamy Retrovirus from Orangutans", Myra O. McClure et al., *Journal of Virology,* vol. 68, No. 11, Nov. 1994, pp. 7124–7130.

"Specific enzyme–linked immunosorbent assay for the detection of antibodies to the human spumavirus", Christoph Mahnke et al., *Journal of Virological Methods,* 29, 1990, pp. 13–22.

*Primary Examiner*—Brian R. Stanton
*Assistant Examiner*—Deborah J. R. Clark

[57] ABSTRACT

The present invention comprises spumavirus isolated from humans. More specifically, the spumavirus of the present invention was isolated from humans who had exposure to nonhuman primates. Importantly, the spumavirus of the present invention or antibodies to the spumavirus can be used to detect the presence of spumavirus or antibodies in body fluids, for pathogenicity studies of related viruses, and as a vector for gene therapies.

4 Claims, 5 Drawing Sheets

SIMIAN FOAMY VIRUS PERCENT NUCLEOTIDE IDENTITY

| | Case1 | Case2 | Case3 | SFV 3 AGM | SFV BAB | SFV MAC | HFV | SFV CPZ | SFV PYG | SFV8 SPM |
|---|---|---|---|---|---|---|---|---|---|---|
| Case1 | - | 82.6 | 82.1 | 87.5 | 82.4 | 77.4 | 68.7 | 66.6 | 67.2 | 66.4 |
| Case2 | - | - | 95.5 | 81.7 | 92.7 | 76.2 | 68.3 | 66.4 | 68.9 | 62.3 |
| Case3 | - | - | - | 82.1 | 93.9 | 76.9 | 67.5 | 66.5 | 69.3 | 62.3 |

FIG. 5

RETROVIRUS ISOLATED FROM HUMANS

TECHNICAL FIELD

The present invention relates to a novel spumavirus that has been definitively isolated from humans.

BACKGROUND OF THE INVENTION

Spumavirus, also known as foamy virus for the characteristics of vacuolization the virus induces in cell culture, belongs to a distinct group of retroviruses. The simian foamy viruses (SFVs) include isolates from Old World and New World monkeys and are classified into 10 different serotypes based on serological cross-reactivities. Virus appears to persist in the host for a long period of time in a latent form and can exist in the presence of neutralizing antibody.

Currently the most studied retrovirus, Human Immunodeficiency Virus, is believed to be derived from nonhuman primate transmission into humans at some past time. Concerns about the risk of transmission of retroviruses from non-human primates to humans working in research laboratories were heightened in the early 1990's when two persons developed antibodies to SIV (Simian Immunodeficiency Virus) following work- related exposures, one of whom had clear evidence of persistent viral infection. (See CDC. Anonymous survey for simian immunodeficiency virus (SIV) seropositivity in SIV laboratory researchers—United States, 1992. MMWR Morb Mort Wkly Rep 1992; 41: 814–5; Khabbaz R. F., et al. Brief report: infection of a laboratory worker with simian immunodeficiency virus. New Eng J. Med. 1994; 330: 172–7; Khabbaz R. F., et al. Simian immunodeficiency virus needlestick accident in a laboratory worker. Lancet 1992; 340: 271–3; and CDC. Guideline to prevent simian immunodeficiency virus infection in laboratory workers and animal handlers. MMWR 1988; 37: 693–704.) In addition to SIV, nonhuman primate species used in biomedical research are commonly infected with SFV (simian foamy virus), STLV (simian t-cell lymphotrophic virus), and/or type D retroviruses. All of these retroviruses cause lifelong infections in nonhuman primates, and some are known to be transmissible through sexual contact, blood, or breast feeding. Natural SFV infections in non-human primates have not been definitively associated with disease. In non-human primates, infection with the other retroviruses may result in a clinical spectrum ranging from asymptomatic infection to life threatening immunodeficiency syndromes or lymphoproliferative disorders. The transmission routes of SFVs among non-human primates remain undefined, but the prevalence of seroreactivity is high among captive adult non-human primates.

Studies of the prevalence of spumavirus infection of humans are limited and the findings are not definitive. Though there is some evidence of human infection with SFV (antibodies and positive PCR results), such occurrence has been reported in only two persons, both of whom had occupational risks for infection. Associated disease was not reported in either. (See Schweizer M., et al. Absence of foamy virus DNA in Graves' disease. AIDS Res & Human Retrov 1994; 10: 601–5; Neumann-Haefelin D., et al., Foamy viruses. Intervirology 1993; 35: 196–207; and Schweizer M., et al., Markers of foamy virus infections in monkeys, apes, and accidentally infected humans: appropriate testing fails to confirm suspected foamy virus prevalence in humans. AIDS Res & Human Retrov 1995; 11: 161–70.) There have been no published reports that virus was ever isolated from these infected individuals.

Other inconclusive evidence was seen in early studies which described a relatively high rate of seroreactivity to antibodies to spumaviruses among human populations not known to be exposed to non-human primates. In some instances seroreactivity was suggestively linked to human disease, including disorders of the central nervous system, thyroid disease, and Chronic Fatigue Syndrome. In most instances these studies lacked definitive evidence of human infection and were not subsequently confirmed. (See Heneine W., et al., Absence of evidence for human spumaretrovirus sequences in patients with Graves' disease [letter]. J Acq Immune Defic Synd & Human Retrov. 1995; 9: 99–101; Simonsen L., et al.,. Absence of evidence for infection with the human spuma retrovirus in an outbreak of Meniere-like vertiginous illness in Wyoming, USA [letter]. Acta Oto-Laryngologica 1994; 114: 223–4; and Heneine W., et al., Lack of evidence for infection with known human and animal retroviruses in patients with chronic fatigue syndrome. Clin Infect Dis 1994; 18: S121–5).

To the knowledge of the inventors, there has not been a documented, definitive isolation of a nonhuman primate origin spumavirus from humans. Previous reports of human spumavirus isolates are now widely regarded as laboratory contaminants.

Recent publications indicate that earlier serological tests showing human spumavirus antibodies in the human population were incorrect. Immunological investigation of a previously reported human spumavirus revealed that it shared common antigens in complement fixation, immunofluorescence and neutralization assays with the chimpanzee foamy virus, SFV-6. Furthermore, failure to detect serological evidence of HFV infection in people from a wide geographical area suggested that this virus isolate was a variant of SFV-6, particularly since sera from chimpanzees naturally infected with SFV-6 neutralized both viruses. In a survey for prevalence of human foamy virus in more than 5000 human sera, collected from geographically diverse populations, none of the serum samples were confirmed as positive. Taken together with sequence analysis endorsing the phylogenetic closeness of the purported human spumavirus to SFV-6/7, these data strongly suggest that human foamy virus is not naturally found in the human population. (See Ali, M. et al., "No Evidence of Antibody to Human Foamy Virus in Widespread Human Populations," AIDS Research and Human Retroviruses, Vol. 12, No. 15, 1996.)

Recent concern that xenotransplantation, the use of living tissues from nonhuman species in humans for medical purposes, may introduce new infections into the human community has increased the importance of defining the ability of simian retroviruses to infect and/or cause disease in humans (See Chapman L. E., et al. Xenotransplantation and xenogeneic infections. New Engl J Med 1995; 333: 1498–1501; DHHS. Docket No. 96M-0311. Draft Public Health Service (PHS) Guideline on Infectious Disease Issues in Xenotransplantation. Federal Register Vol.61, No. 185. Sep. 23, 1996.). The primary animal species considered as donors for xenografts are baboons and pigs. Thus, what is needed are compositions and methods for detecting viruses that may be transmitted from the nonhuman organ donors to the recipient human. Additionally, information regarding these transmissible agents may provide valuable information about the organ donors' cellular receptors that may be important for transplantation success.

Gene therapies have long looked for a good vector that can transport the foreign gene of choice into human cells. The lack of any known disease associated with the virus of the present invention makes the present invention an ideal candidate for gene therapy regimens. Thus, compositions and methods for gene therapy are needed that use a vector capable of carrying a significant amount of foreign DNA that will enter the host organism and not cause disease.

SUMMARY OF THE INVENTION

The present invention is directed to compositions and methods comprising a novel spumavirus. The present invention comprises a spumavirus isolate of human origin that has been definitively isolated from a human with no apparent disease. The novel spuma virus of the present invention has been maintained through tissue culture cells where it causes characteristic vacuolation of the cells. The novel spumavirus of the present invention has utility as a reagent for the immunological screening of the human population for the prevalence of such viruses in the population. The novel spumavirus of the present invention can also serve as a vector in gene therapy because the virus appears to cause no disease in humans and is not transmitted to other humans. Additionally, the novel spumavirus of the present invention can be used as a reagent in pathogenicity studies of these and related viruses. Moreover, the sequences of the novel spumavirus of the present invention can be used as probes to detect virus in biological samples. Vectors include but are not limited to procaryotic, eucaryotic and viral vectors.

The spumaviruses (foamy viruses) are by far the least well characterized of the retroviruses. They have been isolated as agents that cause vacuolation ("foaming") of cells in culture from a number of mammalian species, including monkeys, cattle, cats, and reportedly in humans. Persistent infection with these viruses is not associated with any known disease.

Recent studies using improved diagnostic assays have shown no evidence of foamy virus infection of humans in studies of large populations (approximately 8,000 persons). Given these results, the identification of seroreactivity in three persons occupationally exposed to non-human primates is notable. The PCR identification of viral genome sequences in biologic specimens from all three, and isolation of the virus from one, confirm virus infection in these workers.

The present invention includes the isolation and characterization of a spumavirus that was shown to have been transmitted from non-human primates to humans. The spumavirus of the present invention does not appear to be readily transmitted from human to human. The spumavirus of the present invention can be used in constructing protocols for diagnosing spumavirus infections and may be used as a vector in gene therapy procedures.

The present invention also includes methods and compositions for detecting spumavirus in biological fluids. The methods and compositions, including kits, can be in any configuration well known to those of ordinary skill in the art. The present invention also includes antibodies specific for the spumavirus and antibodies that inhibit the binding of antibodies specific for the spumavirus. These antibodies can be polyclonal antibodies or monoclonal antibodies. The antibodies specific for the spumavirus can be used in diagnostic kits to detect the presence and quantity of spumavirus in biological fluids or in organs from nonhuman primates for xenotransplantation. Antibodies specific for spumavirus may also be administered to a human or animal to passively immunize the human or animal against spumavirus, thereby reducing infection after accidental exposure to nonhuman primate bodily fluids.

The present invention also includes compositions and methods, including kits, for detecting the presence and quantity of antibodies that bind spumavirus in body fluids. The methods, including kits, can be in any configuration well known to those of ordinary skill in the art.

Accordingly, it is an object of the present invention to provide a composition comprising a novel spumavirus.

It is another object of the present invention to provide a method of detecting a spumavirus.

It is yet another object of the present invention to provide methods and compositions for detecting the presence and amount of spumavirus in a body fluid or organ.

A further object of the present invention is to provide compositions and methods for treating genetic and physiologic disorders using gene therapy techniques comprising the novel spumavirus of the present invention as a vector for nucleic acid sequences and antisense sequences.

Another object of the present invention is to provide compositions and methods useful for manipulating the expression of genes.

Yet another object of the invention is to provide vaccines.

Yet another object of the present invention is to provide compositions and methods for treating viral infections in humans or animals.

Another object of the present invention is to provide compositions and methods that are effective in treating genetic diseases.

Yet another object of the present invention is to provide a method of treating microbial infections in humans or animals.

These and other features and advantages of the present invention will become apparent after a review of the following detailed description of the disclosed embodiments and the appended claims.

BRIEF DESCRIPTION OF THE DRAWINGS

FIG. 5 is a comparison of the nucleotide homology of the sequenced portion of the present invention and other retroviruses.

DETAILED DESCRIPTION OF THE INVENTION

Figure 1:
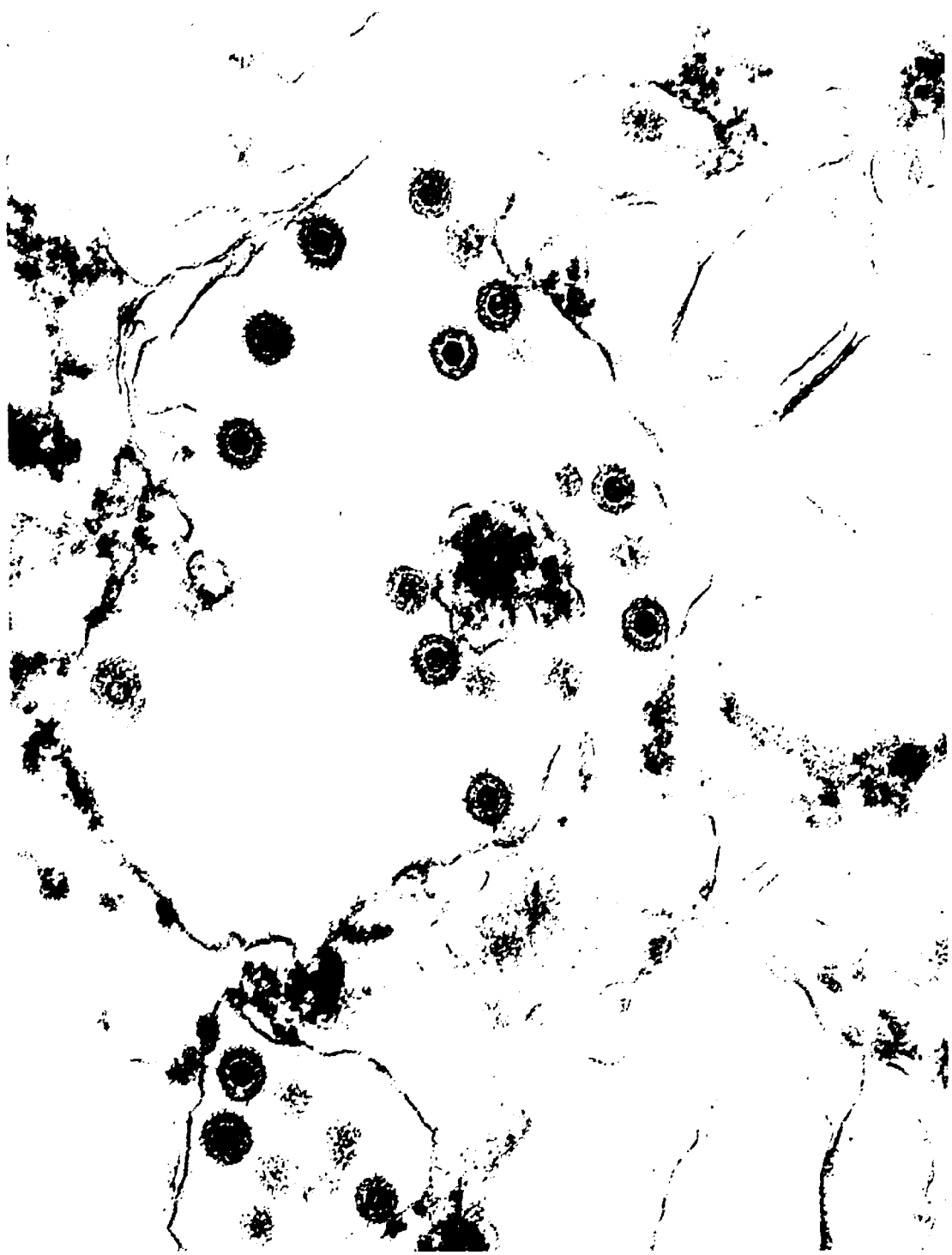
FIG. 1 shows a transmission electron microscope photomicrograph of viral particles in Cf2Th canine thymocytes.

In response to the identification of simian immunodeficiency virus infection in an occupationally exposed workers, Centers for Disease Control and National Institutes for Health collaborated in an anonymous serosurvey of persons with similar work exposures. Simian immunodeficiency virus seroreactivity was present in 3/427 (0.64%) stored serum samples from these anonymous workers (See CDC. Anonymous survey for simian immunodeficiency virus (SIV) seropositivity in SIV laboratory researchers—United States, 1992. MMWR *Morb Mort Wkly Rep* 1992; 41: 814–5; Khabbaz R. F., et al.,. Brief report: infection of a laboratory worker with simian immunodeficiency virus. *New Eng J Med.* 1994; 330: 172–7). Consequently, a voluntary testing and counseling program was developed that allowed linkage between specific exposures or health outcomes and serostatus of persons occupationally exposed to simian immunodeficiency virus. The workers enrolled in this voluntary linked prospective simian immunodeficiency virus surveillance are also at occupational risk for exposure to other retroviruses common in nonhuman primates (non-human primates).

Therefore, in 1995, the linked surveillance was expanded to include voluntary testing and counseling for exposure to simian spumaviruses (more commonly called simian foamy viruses, or SFV), simian T-lymphotropic viruses (STLV), and simian type D retroviruses. 1,823 samples from 13 institutions in the United States had been tested for simian immunodeficiency virus; samples from 231 of the participating volunteer workers were also tested for other retroviruses from non-human primates. Three of these 231 workers (1.3%) were determined to be infected with a SFV-like virus by serology and PCR.

An immunofluorescent assay that was developed using cells infected with SFV serotype 3 identified antibodies to a SFV-like virus in recently collected serum specimens from all three workers. The 3 specimens were also western blot positive, showing reactivity to both p70 and p74 gag precursor bands of SFV-3 antigen. Repeat testing of additional sera obtained from these 3 workers at later time points are also positive in both assays. (These workers or cases are herein identified individually as Case A, Case B, and Case C.)

Additional blood samples from these three cases were tested for SFV proviral DNA sequences using polymerase chain reaction (PCR) assays employing primer sets from two regions of the polymerase gene that are conserved among known primate foamy viruses. All three cases were PCR positive in both regions. The PCR products from one region were sequenced. The sequences from each case were distinct from each other but all showed greater than 80% homology to known non-human primate foamy virus sequences. The partial sequences, produced with DNA polymerase PCR primer, of the viral sequence of the present invention is shown below. Seq. ID 1 is a viral DNA sequence isolated from infected Cf2Th cells and Seq. ID 2 is a viral DNA sequence isolated from PBLs from Case A. There is 99.76% homology between the two sequences. The corresponding RNA sequences and resulting proteins can be deduced from these sequences.

Seq. ID 1

```
TTACTACAAGGACAATATCCAAAAGGTTTTCCAAAACAATATCAATATGA
ACTTAATGAAGGACAAGTTATAGTAACTCGTCCTAATGGACAAAGAATTA
TTCCTCCAAAATCAGACAGGCCTCAAATTATTTTGCAAGCACATAATATT
GCACATACAGGAAGAGATTCAACCTTTCTTAAGGTCTCTTCCAAGTATTG
GTGGCCAAATCTTAGAAAGGATGTGGTTAAAGTTATCAGACAATGTAAGC
AATGTCTGGTCACAAATGCAGCTACCTTAGCTGCGCCTCCAATACTGAGG
CCTGAAAGACCTGTAAAGCCTTTTGATAAATTTTTTGTTGACTATATTGG
CCCTTTACCCCCTTCTAATGGGTACTTACATGTCCTTGTAGTAGTCGATG
GTATGACTGGATTTGTATGGTTA
```

Seq. ID 2

```
TTACTACAAGGACAATATCCAAAAGGTTTTCCAAAACAATATCAATATGA
ACTTAATGAAGGACAAGTTATAGTAACTCGTCCTAATGGACAAAGAATTA
TTCCTCCAAAATCAGACAGGCCTCAAATTATTTTGCAAGCACATAATATT
GCACATACAGGAAGAGATTCAACCTTTCTTAAGGTCTCTTCCAAGTATTG
GTGGCCAAATCTTAGAAAGGATGTGGTTAAAGTTATCAGACAATGTAAGC
AATGTCTGGTCACAAATGCAGCTACCTTAGCTGCGCCTCCAATACTGAGG
CCTGAAAGACCTGTAAAGCCTTTTGATAAATTTTTTGTTGACTATATTGG
CCCTTTACCCCCTTCTAATAGGTACTTACATGTCCTTGTAGTAGTCGATG
GTATGACTGGATTTGTATGGTTA
```

The relationship between each of the isolates and other known spumaviruses is shown in FIG. 5 which is a phylogenetic tree showing the percent homology of the nucleotide sequences of these viruses and in FIG. 6.

Virus isolation was attempted by co-culturing the PBLs (peripheral blood lymphocytes) of Case A with Cf2Th canine thymocytes, a cell line known to be permissive for spumavirus infection. See Mergia A., et al., "Cell tropism of simian foamy virus type 1 (SFV-1)," J. Med. Primatol. 1996: 25: 2–7. Reverse transcriptase activity was detected in co-cultures from the cells exposed to Case A PBLs but not from controls. Transfer of supernatant from the above cells exposed to Case A's PBLs passed this reverse transcriptase activity to uninfected cells, which subsequently showed cytopathic effect (CPE). This finding indicated that the infectious agent in Case A's PBLs was transmitted to tissue culture cells which were used to transfer the infectious agent into other tissue culture cells. Additionally, this indicated that the infectious agent reproduced in the Cf2Th canine thymocytes. DNA-PCR of infected cells was found to be positive for a SFV-like virus. Infected cells showed strong reactivity with all 3 cases' sera by both immunofluorescent assay and western blot and no reactivity with normal sera controls. By electron microscopy, infected Cf2Th cells, derived from cell free supernatants from cells infected by exposure to infected PBLs, showed a morphology characteristic of foamy virus infection (See FIG. 1).

The present invention is directed to compositions and methods comprising a new spumavirus. The virus was isolated from humans who had worked with nonhuman primates. The new spumavirus, or foamy virus, does not appear to cause any disease in the human hosts. The new virus of the present invention may be an excellent vector for gene therapy and for vaccination purposes. Additionally, the antibodies or other detection methods for detecting the new virus may be important in detecting the presence of this and related viruses for xenotransplantation. In addition, the novel spumavirus of the present invention can be used as a reagent in pathogenicity studies of these and related viruses. Moreover, the sequences of the novel spumavirus of the present invention can be used as probes to detect virus in biological samples. Vectors include but are not limited to procaryotic, eucaryotic and viral vectors.

Many new and potentially useful technologies are being developed which use viral vectors and may form the basis of future medical cures and therapies. Examples of such technologies include, but are not limited to, gene replacement, antisense gene therapy, in situ drug delivery, treatment of cancer or infectious agents, and vaccine therapy. However, to be successful, these technologies require an effective means for the delivery of the genetic information across cellular membranes.

The recent advent of technology, and advances in the understanding of the structure and function of many genes makes it possible to selectively turn off or modify the activity of a given gene. Alteration of gene activity can be accomplished many ways. For example, oligonucleotides that are complementary to certain gene messages or viral sequences, known as "antisense" compounds, have been shown to have an inhibitory effect against viruses. By creating an antisense compound that hybridizes with the targeted RNA message of cells or viruses the translation of the message into protein can be interrupted or prevented. In this fashion gene activity can be modulated.

The ability to deactivate specific genes provides great therapeutic benefits. For example, it is theoretically possible to fight viral diseases with antisense molecules that seek out and destroy viral gene products. In tissue culture, antisense oligonucleotides have inhibited infections by herpesviruses, influenza viruses and the human immunodeficiency virus that causes AIDS. It may also be possible to target antisense oligonucleotides against mutated oncogenes. Antisense technology also holds the potential for regulating growth and development. However, in order for the gene therapy to work, antisense sequences must be delivered across cellular plasma membranes to the cytosol.

Gene activity is also modified using sense DNA in a technique known as gene therapy. Defective genes are replaced or supplemented by the administration of "good" or normal genes that are not subject to the defect. Instead of being defective, the gene have been deleted, thus replacement therapy would provide a copy of the gene for use by the cell. The administered normal genes can either insert into a chromosome or may be present as extracellular DNA and can be used to produce normal RNA, leading to production of the normal gene product. In this fashion gene defects and deficiencies in the production of a gene product may be corrected.

Still further gene therapy has the potential to augment the normal genetic complement of a cell. For example, it has been proposed that one way to combat HIV is to introduce into an infected person's T cells a gene that makes the cells resistant to HIV infection. This form of gene therapy is sometimes called "intracellular immunization." Genetic material such as a polynucleotide sequence may be administered to a mammal in a viral vector to elicit an immune response against the gene product of the administered nucleic acid sequence. Such gene vaccines elicit an immune response in the following manner. First, the viral vector containing the nucleic acid sequence is administered to a human or animal. Next, the administered sequence is expressed to form a gene product within the human or animal. The gene product inside the human or animal is recognized as foreign material and the immune system of the human or animal mounts an immunological response against the gene product. The virus of the present invention may be used as a viral vector to provide the foreign nucleic acid sequences to the intracellular metabolic processes.

Additionally, gene therapy may be used as a method of delivering drugs in vivo. For example, if genes that code for therapeutic compounds can be delivered to endothelial cells, the gene products would have facilitated access to the blood stream. Additionally, cells could be infected with a retroviral vector such as the present invention carrying nucleic acid sequences coding for pharmaceutical agents that prevent infection from occurring in the retrovirally infected cells.

The novel spuma virus of the present invention can also be used a safe and effective vaccine agent. Genetic sequences for immunogenic proteins from a variety of infectious agents can be incorporated into the foamy virus RNA. Once inside a cell, the gene product is expressed and releases the immunizing peptide to the body's immune system. In another method, the virus of the present invention can be used to immunize the body against cell markers found on cancer or tumor cells. The genetic sequence of the cancer cell marker is incorporated into the foamy virus RNA and after infection with the virus, the expressed gene product stimulates the immune system. The patient's immune system is used to remove the cancerous cells, obviating the need for chemotherapeutic methods.

The antibodies of the present invention can be used to detect the presence of the virus or viral particles of the present invention. These antibodies can be used in diagnostic or screening kits to assess the present of the virus. Additionally, the antibodies can be used to screen organs from nonhuman primates that may be used in humans. Detection of the presence of a virus that is transmitted from nonhuman primates to humans would be crucial in providing virus-free organs for transplantation.

The inventors of the present invention believe that the virus of the present invention, comprising the isolates from Cases A, B, and C, and particularly Case A, are the first definitive isolation of an SFV-3-like spumavirus from persons exposed to nonhuman primates. The virus does not appear to cause disease and does not appear not transmitted to close household contacts or sexual contacts. This belief is supported by the epidemiology data, the PCR and sequencing data and the serology data.

A spumavirus of the present invention was deposited with the American Type Culture Collection under the provisions of the Budapest Treaty. The deposit was made Feb. 5, 1998. The address of the American Type Culture Collection is 10801 University Boulevard, Manasses, Va. 20110-2209. The deposited spumavirus is taxonomically known as SFV-Hu1, and comprises the sequences disclosed herein. The deposited spumavirus was assigned ATCC VR-2596 by the American Type Culture Collection.

The present invention is further described by the examples which follow. Such examples, however, are not to be construed as limiting in any way either the spirit or scope of the present invention. In the examples, all parts are parts by weight unless stated otherwise.

EXAMPLE 1

Case A

Case A has intermittently been employed as a caretaker for non-human primates for twenty years between 1961 and 1997. Case A recalled multiple minor injuries and mucocutaneous exposures to non-human primate blood, body fluids, or fresh tissue. In addition, Case A was twice bitten by African green monkeys in the 1960s or early 70s. These injuries were severe enough to require 7–10 stitches each. Case A is single and in good health. No sera collected from Case A prior to 1995 or from sexual partners are currently available for testing. Retrospective analysis of sera archived from Case A in 1995 showed the sera to have antibodies to SFV. (See FIG. 3, lane 2).

Figure 3:
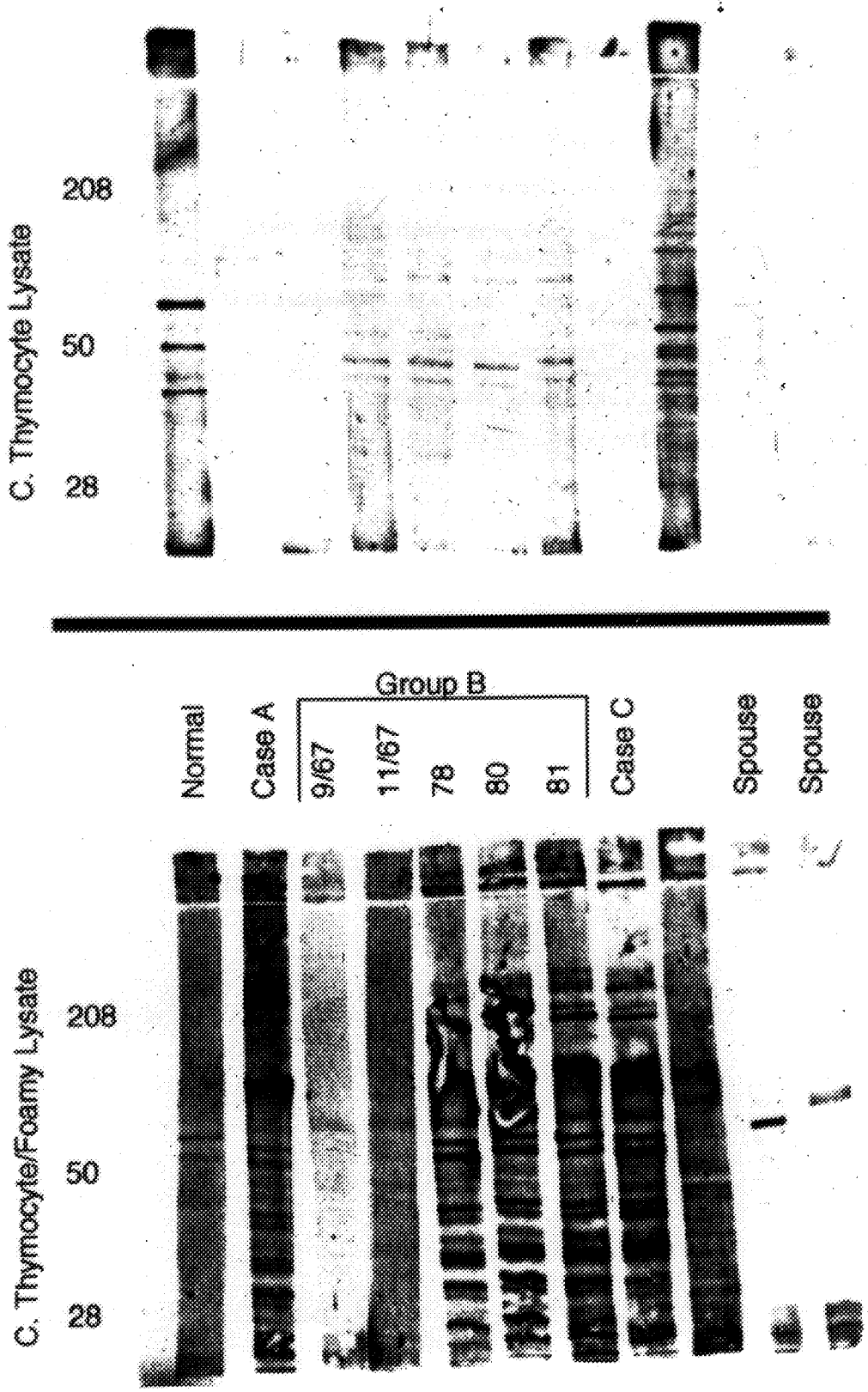
FIG. 3 is a Western blot of sera from Case A, Case B and Case C and the sera of spouses of two of the cases. The sera was tested against the whole cell lysate from Cf2Th cells infected with the spumavirus isolate. Whole cell lysate of uninfected Cf2Th were used as a control for seroreactivity towards nonviral proteins. In addition, the sera of Case B provides a view of the history of infection because of the existence of Case B sera obtained in 1967, and in 1978, 1980, and 1981.
Figure 4:
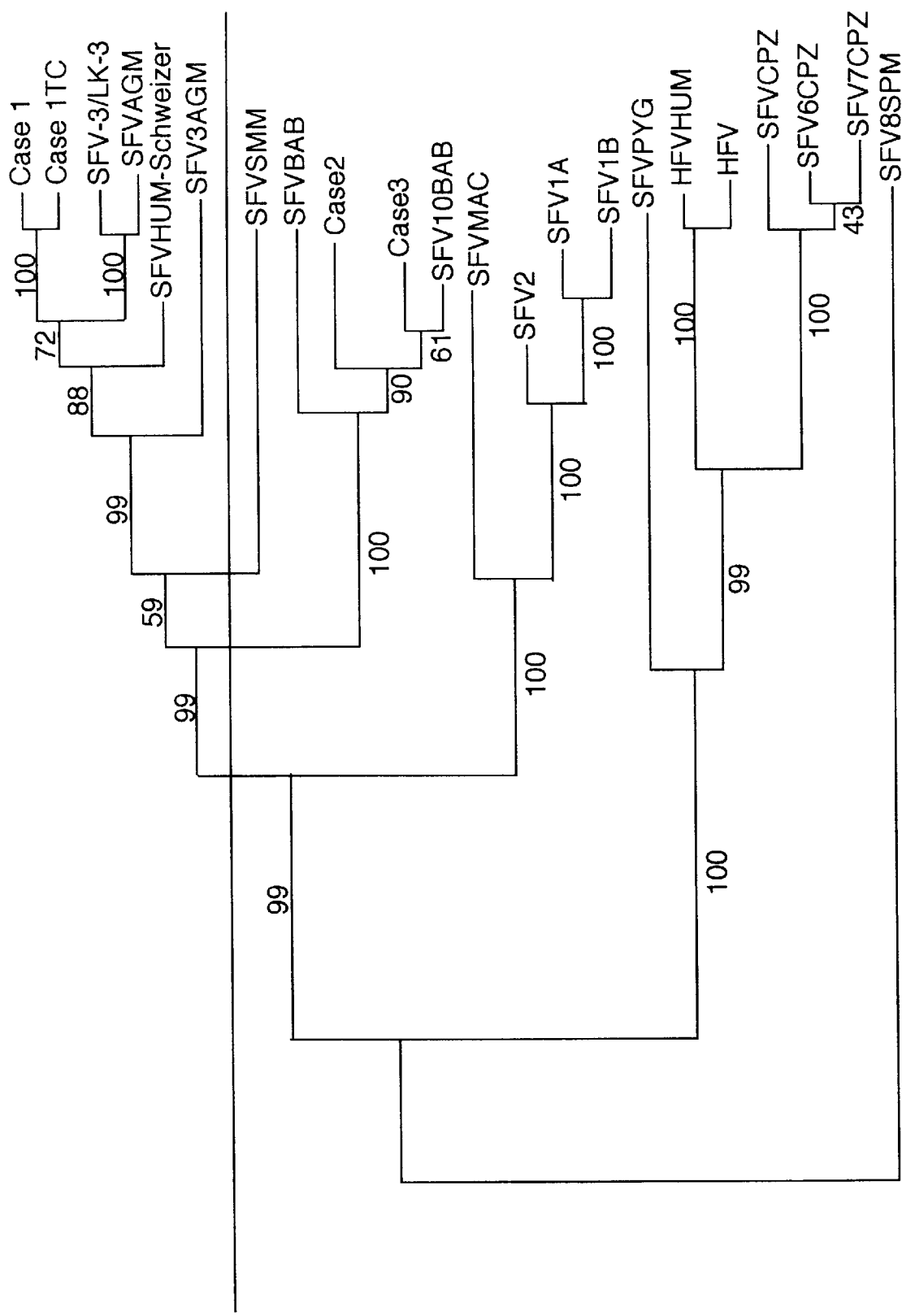
FIG. 4 is a phylogenetic tree showing the relationships between the sequences of the viruses of the novel spumavirus of the present invention and known spumaviruses.

The western blot of FIG. 3 shows whole cell lysate from Cf2Th cells infected with the spumavirus of the present invention tested in each individual lane with different antisera. In FIG. 3, particular viral proteins that show infection are the proteins with molecular weight of approximately 70–80 Daltons (p70 gag protein) and the proteins at approximately 130–140 Daltons (an envelope protein). The western blot of FIG. 3 shows whole cell lysate from Cf2Th cells infected with the spumavirus of the present invention. These proteins are not detectable in the western blot of FIG. 3 by normal sera, (lane 1) but are detectable by antisera from Case A.

EXAMPLE 2

Case B

Case B is a research scientist employed for three decades working with biologic specimens from non-human primates. Case B rarely reported injuries involving non-human primate blood, body fluids, or unfixed tissue, but did report an injury in 1970 when an unused needle was stuck through a glove that was potentially contaminated with baboon body fluids; and a 1972 cut inflicted by a broken capillary tube containing chimpanzee blood. Case B is in good health. Case B has been in a monogamous sexual relationship without use of barrier contraceptives or spermicides for over 20 years. Case B's spouse is negative for SFV-like infection by both serologic and PCR testing. Analysis of two serum specimens from Case B archived serially in 1967 were negative; sera archived in 1978 and subsequently were consistently seropositive. See FIG. 3, lanes 3 and 4 are the 1967 sera, lane 5 is sera from 1978, lane 6 is sera from 1980, lane 7 is sera from 1981. The sera of Case B's spouse is shown in lane 10.

EXAMPLE 3

Case C

Case C is an animal care supervisor who has worked with non-human primates for more than 3 decades. Case C recalls multiple minor injuries and mucocutaneous exposures to non-human primate blood, body fluids, or unfixed tissues. Case C reported a severe baboon bite around 1980 that required multiple stitches of an arm and hand. Case C is in good health except for type II diabetes mellitus. Case C has been in a monogamous sexual relationship for nearly three decades, during which barrier methods of contraception have not been employed and spermicides were used for no more than a 6 month period. Case C's spouse is negative for SFV-like infection by both serologic and PCR testing. Retrospective analysis of sera archived from Case C in 1988 showed the sera to have antibodies to SFV. See FIG. 3, lane 8 is Case C's sera from 1988, and lane 11 is sera from the spouse of Case C.

EXAMPLE 4

Western Blot Analysis

The sera from the three cases was analyzed by western blot analysis against whole cell lysates from Cf2Th cells infected by cell free supernatants from Cf2Th cells infected by a Case's PBLs. As shown in FIG. 3, Case A, Case B and Case C all show the characteristic gag proteins associated with the spumavirus. It is interesting to note that in Case B, Case B converted from negative to positive between 1967 and 1978. In addition, spouses of two of the Cases were negative.

EXAMPLE 5

Simian Foamy Virus Isolation

Peripheral blood lymphocytes (PBLs) were isolated from Cases A, B and C and were cultured with IL-2 for 48 hours, in RPI media with 10% fetal Calf serum, and penn-strep antibiotics. After 48 hours, the PBLs were added to the Cf2Th cells and co-cultured for 2–4 weeks. The cells were in DMEM supplemented with 2% nonessential amino acids, 20% fetal calf serum, and pen-strep antibiotics. 1 mL supernatants were collected from the cell cultures every 3 to 4 days and tested for amp-reverse transcriptase. Procedures for PBL treatment, culturing of Cf2Th cells and amp reverse transcriptase activity were procedures known to those in the art. For example, see Heneine, W., et al. "Detection of reverse transcriptase by a highly sensitive assay in sera from persons infected with HIV-1." (1995). J. infectious Diseases, 171: 1201–6.

EXAMPLE 6

Because of the positive amp-reverse transcriptase activity from cells from Case A, peripheral blood lymphocytes from Case A were cultured with IL-2 for 48 hours prior to addition to canine thymocytes (Cf2Th), human lung fibroblasts, and normal human peripheral blood lymphocytes. Supernatants were collected every 3 to 4 days and tested for amp-reverse transcriptase activity. Each time the 1 mL sample of supernatant was taken for amp-reverse transcriptase activity, a 5 mL sample of supernatant was taken and frozen at −80° C. in order to preserve a sample of the virus producing the amp-reverse transcriptase activity.

Figure 2:
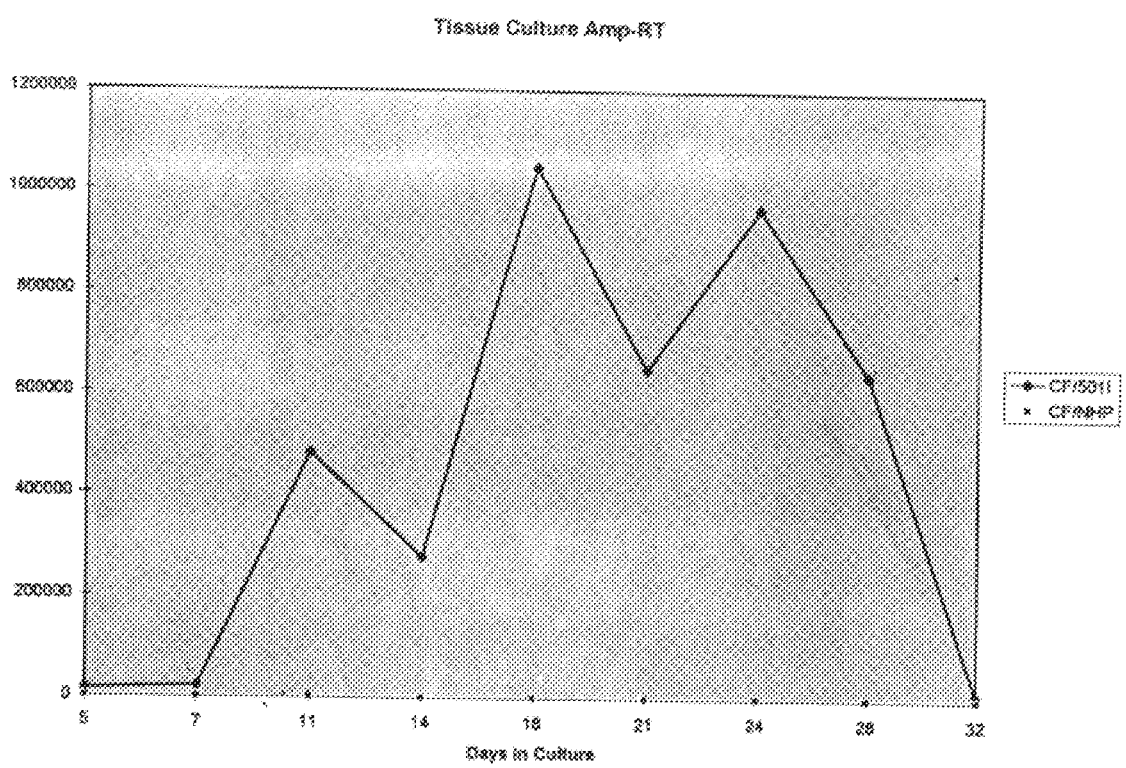
FIG. 2 shows tissue culture AMP-reverse transcriptase activity in canine thymocyte cells (Cf2Th) co-cultured with peripheral blood lymphocytes from an infected case worker. Along the baseline is another line showing control Cf2Th cells that were co-cultured with normal human peripheral blood lymphocytes, indicating there was no constitutive reverse transcriptase activity in these cultures.

At day 5, amp-reverse transcriptase testing showed a slightly positive signal in the canine thymocyte culture. The amp-reverse transcriptase activity increased over time. (See FIG. 2).

The activity in control Cf2Th cells that were treated as above, except for exposure to normal PBLs instead of infected PBLs, was shown by the lower line that overlaps the baseline. There was no amp-reverse transcriptase activity inherently in these Cf2Th cells, providing evidence that there was no contamination by a retrovirus or spumavirus by the tissue culture cells.

EXAMPLE 7

At the peak of amp-reverse transcriptase activity as described in Example 5, cell-free supernatants were transferred to fresh Cf2Th growing at $2\times10^5$ cells/mL. At day 4 in the new culture, cytopathic effects and syncytia was observed. Transmission electron microscopy showed viral particles in and around the cells (See FIG. 1). Viral particles were isolated from these cultures and were stored at the Centers for Disease Control and will be deposited at the ATCC.

The Cf2Th cells were obtained from the in-house cell culture facility of the Centers for Disease Control, but these cells can also be obtained from the American Type Culture Collection (Rockville, Md.). See Mergia et al., et al., "Cell tropism of the simian foamy virus type 1 (SFV-1)," J. Med. Primatol. 1996: 25: 2–7, for use of these cells.

Having thus described the invention, numerous changes and modifications thereof will be readily apparent to those having ordinary skill in the art, without departing from the spirit or scope of the invention.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 423 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

```
TTACTACAAG  GACAATATCC  AAAAGGTTTT  CCAAAACAAT  ATCAATATGA  ACTTAATGAA       60
GGACAAGTTA  TAGTAACTCG  TCCTAATGGA  CAAAGAATTA  TTCCTCCAAA  ATCAGACAGG      120
CCTCAAATTA  TTTTGCAAGC  ACATAATATT  GCACATACAG  GAAGAGATTC  AACCTTTCTT      180
AAGGTCTCTT  CCAAGTATTG  GTGGCCAAAT  CTTAGAAAGG  ATGTGGTTAA  AGTTATCAGA      240
CAATGTAAGC  AATGTCTGGT  CACAAATGCA  GCTACCTTAG  CTGCGCCTCC  AATACTGAGG      300
CCTGAAAGAC  CTGTAAAGCC  TTTTGATAAA  TTTTTTGTTG  ACTATATTGG  CCCTTTACCC      360
CCTTCTAATG  GGTACTTACA  TGTCCTTGTA  GTAGTCGATG  GTATGACTGG  ATTTGTATGG      420
TTA                                                                        423
```

( 2 ) INFORMATION FOR SEQ ID NO:2:

( i ) SEQUENCE CHARACTERISTICS:
        ( A ) LENGTH: 423 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

```
TTACTACAAG  GACAATATCC  AAAAGGTTTT  CCAAAACAAT  ATCAATATGA  ACTTAATGAA       60
GGACAAGTTA  TAGTAACTCG  TCCTAATGGA  CAAAGAATTA  TTCCTCCAAA  ATCAGACAGG      120
CCTCAAATTA  TTTTGCAAGC  ACATAATATT  GCACATACAG  GAAGAGATTC  AACCTTTCTT      180
AAGGTCTCTT  CCAAGTATTG  GTGGCCAAAT  CTTAGAAAGG  ATGTGGTTAA  AGTTATCAGA      240
CAATGTAAGC  AATGTCTGGT  CACAAATGCA  GCTACCTTAG  CTGCGCCTCC  AATACTGAGG      300
```

-continued

| | | | | | | |
|---|---|---|---|---|---|---|
| CCTGAAAGAC | CTGTAAAGCC | TTTTGATAAA | TTTTTGTTG | ACTATATTGG | CCCTTTACCC | 360 |
| CCTTCTAATA | GGTACTTACA | TGTCCTTGTA | GTAGTCGATG | GTATGACTGG | ATTTGTATGG | 420 |
| TTA | | | | | | 423 |

What is claimed:

1. A spumavirus isolated from a human and cross-reactive with SFV-3 antibodies, the spumavirus having ATCC Deposit No. ATCC VR-2596.

2. A vector comprising a sequence from a spumavirus isolated from a human and cross-reactive with SFV-3 antibodies, the spumavirus having ATCC Deposit No. ATCC VR-2596, wherein the sequence comprises Seq. ID. 1 or Seq. ID. 2.

3. The vector of claim 2, wherein the sequence comprises Seq ID. 1.

4. The vector of claim 2, wherein the sequence comprises Seq ID. 2.

* * * * *